(12) United States Patent
Sargent, Jr. et al.

(10) Patent No.: US 8,449,492 B2
(45) Date of Patent: May 28, 2013

(54) APPLICATOR HAVING AN ENHANCED GRIPPING REGION

(75) Inventors: Raymond Albert Sargent, Jr., Mason, OH (US); Devin William Baldridge, Cincinnati, OH (US); David Andrew Dalton, Loveland, OH (US); Richard Perez, Cincinnati, OH (US); Margaret Henderson Hasse, Wyoming, OH (US); Diana Lynn Gann, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 77 days.

(21) Appl. No.: 13/240,098

(22) Filed: Sep. 22, 2011

(65) Prior Publication Data

US 2012/0016288 A1    Jan. 19, 2012

Related U.S. Application Data

(63) Continuation of application No. 11/786,837, filed on Apr. 13, 2007, now Pat. No. 8,075,512.

(51) Int. Cl.
*A61F 13/02* (2006.01)
*A61F 13/20* (2006.01)

(52) U.S. Cl.
USPC ............................. 604/15; 424/431

(58) Field of Classification Search
USPC ............. 604/11, 15, 385.17, 385.18; 424/431
See application file for complete search history.

(56) References Cited

U.S. PATENT DOCUMENTS

| | | | |
|---|---|---|---|
| 1,224,735 A | 5/1917 | Gamache, Jr. et al. | |
| 2,922,423 A | 1/1960 | Rickard et al. | |
| 3,575,169 A | 4/1971 | Voss et al. | |
| 4,048,998 A | 9/1977 | Nigro | |
| 4,198,978 A | 4/1980 | Nigro | |
| 4,411,647 A | 10/1983 | Sakurai et al. | |
| 5,087,239 A | 2/1992 | Beastall et al. | |
| 5,158,535 A | 10/1992 | Paul et al. | |
| 5,681,894 A | 10/1997 | Williams et al. | |
| 5,709,652 A | 1/1998 | Hagerty | |
| 5,738,646 A | 4/1998 | Fox et al. | |
| 5,931,803 A | 8/1999 | Jackson | |
| 6,019,743 A | 2/2000 | Cole et al. | |
| 6,019,744 A | 2/2000 | Altdorf et al. | |
| 6,264,626 B1 | 7/2001 | Linares et al. | |
| 6,416,488 B1 | 7/2002 | Jackson et al. | |
| 6,423,025 B1 | 7/2002 | Buzot | |

(Continued)

FOREIGN PATENT DOCUMENTS

| | | |
|---|---|---|
| EP | 0 064 747 A2 | 11/1982 |
| EP | 0 213 241 A1 | 3/1987 |
| EP | 0 597 446 B1 | 4/1998 |
| GB | 2166656 B | 6/1988 |

OTHER PUBLICATIONS

U.S. Appl. No. 11/786,837, filed Apr. 13, 2007, Office Actions from Mar. 25, 2010 to Sep. 2, 2011.

*Primary Examiner* — Melanie Hand
(74) *Attorney, Agent, or Firm* — Andrew J. Hagerty

(57) ABSTRACT

An applicator having an enhanced grip portion. The applicator can include a barrel portion having an insertion end, a withdrawal end, and a barrel exterior surface, the barrel exterior surface being a barrel color, a grip portion positioned opposite the insertion end having a grip exterior surface, and a plunger having a plunger exterior surface. The applicator can further include gripping indicia disposed substantially on the grip exterior surface. The gripping indicia can include visual indicia and/or tactile indicia.

10 Claims, 2 Drawing Sheets

U.S. PATENT DOCUMENTS

| | | |
|---|---|---|
| 6,572,577 B1 | 6/2003 | Binner et al. |
| 6,648,846 B2 | 11/2003 | Binner et al. |
| 6,730,057 B2 | 5/2004 | Zhao et al. |
| 6,830,554 B2 | 12/2004 | Jackson et al. |
| 6,890,324 B1 | 5/2005 | Jackson et al. |
| 6,923,789 B2 | 8/2005 | LeMay et al. |
| 6,946,585 B2 | 9/2005 | London Brown |
| 7,014,637 B1 | 3/2006 | Denti et al. |
| 7,044,928 B2 | 5/2006 | LeMay et al. |
| 7,172,573 B1 | 2/2007 | Lamb |
| 7,217,252 B2 | 5/2007 | Swick |
| 7,704,242 B2 | 4/2010 | LeMay et al. |
| 7,727,208 B2 | 6/2010 | LeMay et al. |
| 2002/0010413 A1 | 1/2002 | Binner et al. |
| 2002/0143287 A1 | 10/2002 | Buzot |
| 2003/0073947 A1 | 4/2003 | Binner et al. |
| 2003/0073948 A1 | 4/2003 | Binner et al. |
| 2003/0216680 A1 | 11/2003 | Binner et al. |
| 2003/0236485 A1 | 12/2003 | Fedyk et al. |
| 2004/0010220 A1 | 1/2004 | Miller et al. |
| 2004/0050738 A1 | 3/2004 | Molina et al. |
| 2004/0199102 A1 | 10/2004 | LeMay et al. |
| 2005/0096617 A1 | 5/2005 | Gorham et al. |
| 2005/0154365 A1 | 7/2005 | Zander et al. |
| 2005/0171463 A1 | 8/2005 | Suga |
| 2005/0197617 A1 | 9/2005 | Gorham et al. |
| 2006/0135905 A1 | 6/2006 | Miller et al. |
| 2006/0167431 A1 | 7/2006 | Denti et al. |
| 2006/0258971 A1 | 11/2006 | Chase et al. |
| 2007/0032758 A1 | 2/2007 | Chase et al. |
| 2007/0156080 A1 | 7/2007 | Loyd et al. |
| 2007/0167902 A1 | 7/2007 | Edgett et al. |
| 2008/0033337 A1 | 2/2008 | Dougherty, Jr. et al. |
| 2008/0167597 A1 | 7/2008 | Dougherty |
| 2008/0255496 A1 | 10/2008 | Sargent et al. |
| 2010/0016780 A1 | 1/2010 | Vandenbogart et al. |
| 2011/0105830 A1 | 5/2011 | Hou et al. |

APPLICATOR HAVING AN ENHANCED GRIPPING REGION

CROSS REFERENCE TO RELATED APPLICATIONS

This application is a continuation of U.S. application Ser. No. 11/786,837 filed Apr. 13, 2007 now U.S. Pat. No. 8,075,512.

FIELD OF THE INVENTION

The present invention relates generally to applicators having an enhanced gripping region, more specifically to applicators for feminine hygiene products.

BACKGROUND OF THE INVENTION

Feminine care products, such as tampons and pessaries, are generally used by women within the vagina, such as, e.g., to absorb menstrual or other body exudates, for pelvic support, and/or for other feminine needs. Such feminine products can be inserted into the vagina digitally, such as, e.g., by using a finger, or can be inserted into the vagina by using an applicator.

Applicators typically comprise an insertion member and a plunger. The material to be expelled from the applicator, such as an absorbent tampon or pessary, can be positioned within the insertion member. The insertion member can have a first end for insertion of the material and a second end for receipt of the plunger. To use the applicator, the consumer will grasp the insertion member, position the first end appropriately, such as, e.g., into the body, and move the plunger in the insertion member towards the first end to insert the material. Some applicators can also include a fingergrip portion that is located on or adjacent to the insertion member, which can allow the consumer to more securely hold the applicator during insertion of a material into the body cavity.

Various fingergrip configurations have been utilized to facilitate the handling of the applicator and to improve the insertion experience. Currently available configurations, however, are not yet optimized to consistently deliver such benefits. For example, currently available feminine care applicators are generally uniform in color and material with a fingergrip portion that may have a raised and/or depressed grip configuration. As such, the fingergrip portion may not be easily distinguishable from the remainder of the insertion member. If the fingergrip portion is not easily identifiable, the user may place her fingers incorrectly on the applicator, which may result in an unsteady grip, improper insertion, soiled fingertips, finger slippage, or an otherwise undesirable usage experience.

As such, it would be desirable to provide an applicator having an enhanced grip portion.

SUMMARY OF THE INVENTION

An applicator having an enhanced grip portion is provided. The applicator can include a barrel portion having an insertion end, a withdrawal end, and a barrel exterior surface, the barrel exterior surface being a barrel color, a grip portion positioned opposite the insertion end having a grip exterior surface, and a plunger having a plunger exterior surface. The applicator can further include gripping indicia disposed substantially on the grip exterior surface. The gripping indicia can include visual indicia and/or tactile indicia.

An array of applicators is also provided.

DETAILED DESCRIPTION OF THE INVENTION

Figure 1:
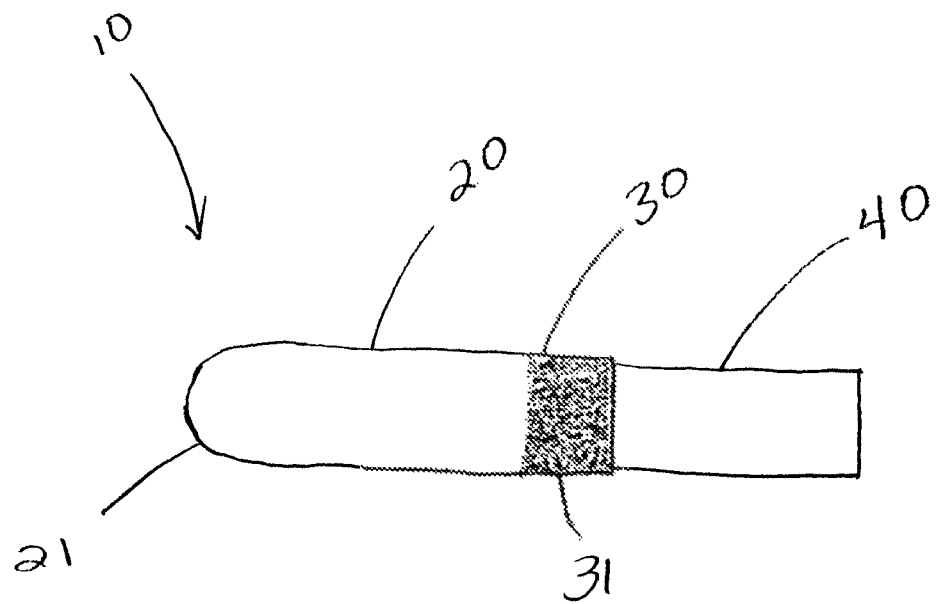
FIG. 1 is a side view of an applicator of the present invention.

Applicators having an enhanced grip portion are provided. The enhanced grip portion can have one or more gripping indicia. In certain embodiments, the gripping indicia can be visual indicia. In addition, or alternatively, the enhanced grip portion can have one or more tactile indicia. Such an enhanced grip portion can provide a user with visual and/or tactile indicia of proper finger placement during use of the applicator, as well as visual and/or tactile indicia communicating improved performance, secure handling, reduction of finger slippage, clean insertion, consistent placement, depth of insertion, proper orientation, and/or one or more auditory signals.

As used herein, the term "feminine care product" includes absorbent articles useful for feminine needs, such as articles that typically can be intended for feminine use internally, such as, e.g., within a user's vagina. Internal feminine care products can include, for example, tampons and pessaries.

As used herein, the term "tampon" refers to any type of absorbent structure that can be inserted into the vaginal canal or other body cavity, such as, e.g., for the absorption of fluid, to aid in wound healing, and/or for the delivery of materials, such as moisture or active materials such as medicaments.

As used herein, the term "pessary" refers to any type of substantially non-absorbent structure for the purpose of reducing urine leakage and/or supporting a prolapsed uterus and/or bladder. Such pessaries can have any variety of shapes and sizes including cylinder, ovate, spherical, tubular, annual rings, "U" shaped, cup shaped, rings, cubes or donut shaped, and can function in any suitable manner, such as, e.g., by direct application of support, lever force, expansion of the device by selection of material, and/or by inflation of the device.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, "applicator" refers to a device or implement that facilitates the insertion of a feminine care product, such as, e.g., a tampon or pessary, into an external orifice of a mammal. Suitable applicators include, e.g., telescoping, tube and plunger, and compact applicators.

As used herein, the term "insertion end" refers to the portion of the tampon or applicator including the end that is intended to enter the vaginal canal first when inserting the tampon or applicator into the vaginal canal.

As used herein, the term "withdrawal end" refers to the portion of the applicator opposite the insertion end.

As used herein, the term "gripping structures" refers to raised or depressed structures provided at the grip portion of the applicator that can assist a user in grasping the applicator. In certain embodiments, gripping structures can be raised or depressed relative to the surface of the grip portion.

As used herein, the term "gripping indicia" refers to indicia, such as, e.g., indicia located on or adjacent the grip portion of an applicator, that can indicate to the user information relating to the grip portion, such as, e.g., visual indicia and/or tactile indicia. In certain embodiments, gripping indicia can communicate to a user information, such as, e.g., by defining the grip portion from the barrel and/or plunger portion, distinguishing absorbency of the material disposed within the applicator, increasing usage enjoyment, instructing a user where to place her fingers during use of the applicator, indicating to a user when to stop inserting the applicator, and/or by showing a user how to properly orient an applicator, such as, e.g., an applicator having a non-circular cross-sectional shape and/or an applicator containing material with more expansion in a direction, such as, e.g., width-wise expansion. In addition, or alternatively, gripping indicia can facilitate improved control and decreased finger slippage.

As used herein, the term "visual indicia" refers to one or more indications or a signal visually perceptible to the user that corresponds to the grip portion. Visual indicia can be only visually perceptible, i.e., a visually perceptible visual indicia, or can be visually perceptible and tactilely perceptible. By "visually perceptible" is meant that a human viewer can visually discern the visual indicia with the unaided eye (excepting standard corrective lenses adapted to compensate for nearsightedness, farsightedness, or astigmatism, or other corrected vision) in lighting at least equal to the illumination of a standard 100 watt incandescent white light bulb at a distance of 1 meter. By "only visually perceptible" is meant that the visual indicia cannot be readily perceived by touch. Therefore, gripping formations, embossments, raised printing, and the like are generally not considered to be only visually perceptible. However, one or more visual indicia that are only visually perceptible can be used in conjunction with such gripping formations, tactilely perceptible embossments, raised printing, and the like. For example, one or more visually perceptible visual indicia can be used in conjunction with one or more gripping formations.

As used herein, the term "tactile indica" refers to one or more indications or a signal tactilely perceptible to the user that corresponds to the grip portion. Tactile indica can be visually perceptible and/or tactilely perceptible. In certain embodiments, tactile indica can be substantially only tactilely perceptible, i.e., a tactilely perceptible tactile indicia. By "tactilely perceptible" is meant that a user can perceive the indicia by touch. By "only tactilely perceptible" is meant that the tactile indicia cannot be readily perceived visually, such as, e.g., a tactile indicia that can increase the coefficient of friction on a grip portion compared to the coefficient of friction on a barrel portion of an applicator and/or a compressible material, such as, e.g., rubber, silicone, and/or foam. As such, typically used gripping structures would not be only tactilely perceptible. Of course, one or more visual indicia can be used with one or more tactile indicia that are only tactilely perceptible. For example, one or more tactilely perceptible tactile indicia can be used in conjunction with one or more colors.

As used herein, the term "color" includes any color, such as, e.g., white, black, red, orange, yellow, green, blue, violet, brown, and/or any other color.

FIG. 1 shows one embodiment of an applicator 10. The applicator 10 comprises a barrel portion 20, a grip portion 30, and a plunger 40. The barrel portion 20 has an insertion end 21. The grip portion 30 is disposed opposite the insertion end 21 of the barrel portion 20. As shown in FIG. 1, the grip portion 30 contains gripping indicia 31. In this embodiment, the gripping indicia 31 can be a visual indicia that is a color different from the color of the barrel portion 20, such as, e.g., a blue gripping indicia 31 and a white barrel portion 20. In certain embodiments, the gripping indicia 31 can communicate to a user where the grip portion 30 is located on the applicator 10, which can assist the user in proper placement of her fingers on the grip portion 30 and/or can increase the user's confidence in proper handling of the applicator 10. In addition, or alternatively, the gripping indicia 31 can communicate to a user the identity and/or absorbency of material disposed within the applicator 10, can indicate to a user when the applicator is fully inserted, and/or can increase user enjoyment. In certain embodiments, the gripping indicia 31 can show a user how to properly orient an applicator, such as, e.g., an applicator having a non-circular cross-sectional shape and/or an applicator containing material with more expansion in a direction, such as, e.g., width-wise expansion.

Figure 2:
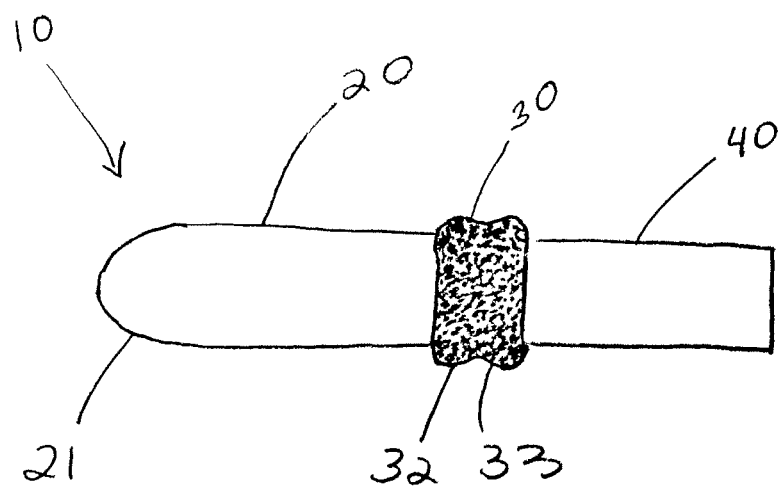
FIG. 2 is a side view of an applicator of the present invention.

FIG. 2 shows one embodiment of an applicator 10. The applicator 10 comprises a barrel portion 20, a grip portion 30, and a plunger 40. The barrel portion 20 has an insertion end 21. The grip portion 30 is disposed opposite the insertion end 21 of the barrel portion 20. As shown in FIG. 2, the grip portion 30 contains gripping indicia 31 that can include a visual indicia 32 and a tactile indicia 33. In this embodiment, the visual indicia 32 can be a color different from the color of the barrel portion 20 and the tactile indicia 33 can be a compressible material. In certain embodiments, the visual indicia 32 can communicate to a user where the grip portion 30 is located on the applicator 10 and/or can increase the user's confidence in proper handling of the applicator 10. In addition, or alternatively, the tactile indicia 33 can communicate to a user the location of the grip portion 30, such as, e.g., by feel, can increase user comfort, and/or can communicate a perception of security and improved handling to the user.

Figure 3:
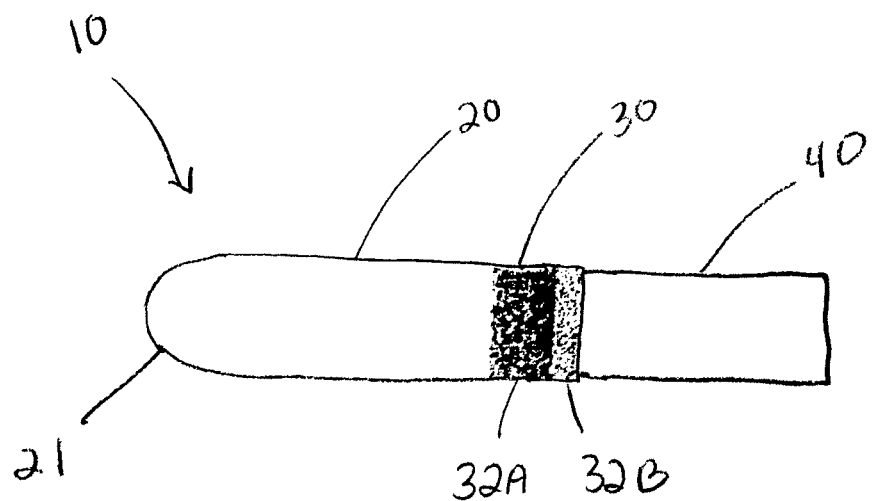
FIG. 3 is a side view of an applicator of the present invention.

FIG. 3 shows one embodiment of an applicator 10. The applicator 10 comprises an barrel portion 20 and a plunger 30. The barrel portion 20 has an insertion end 21 and a grip portion 30 opposite the insertion end 21. As shown in FIG. 3, the grip portion 30 contains gripping indicia 31 that can be a first visual indicia 32A and a second visual indicia 32B. In this embodiment, the first visual indicia 32A is a color different from the color of the barrel portion 20 and the second visual indicia 32B is a color different from the color of the barrel portion 20 and of the color of the first visual indicia 32A. In certain embodiments, the first visual indicia 32A can communicate to a user where the grip portion 30 is located on the applicator 10, which can assist the user in proper placement of her fingers on the grip portion 30 and/or can increase the user's confidence in proper handling of the applicator 10. In certain embodiments, the second visual indicia 32B can communicate key aspects and/or elements of the grip portion 30 to the user, such as, e.g., by highlighting certain areas of the grip portion.

Figure 4:
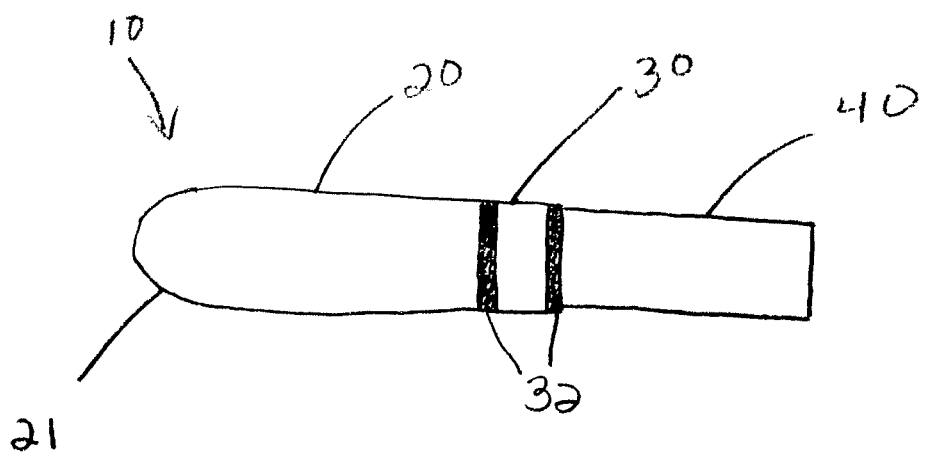
FIG. 4 is a side view of an applicator of the present invention.

FIG. 4 shows one embodiment of an applicator 10. The applicator 10 comprises an barrel portion 20 and a plunger 30. The barrel portion 20 has an insertion end 21 and a grip portion 30 opposite the insertion end 21. As shown in FIG. 4, the grip portion 30 contains gripping indicia 31 that can be one or more visual indicia 32. In this embodiment, the visual indicia 32 is in the form of a colored line different from the color of the barrel portion 20 and the color of the grip portion 30. In certain embodiments, the visual indicia 32 can communicate to a user where the grip portion 30 is located on the applicator 10, which can assist the user in proper placement of her fingers on the grip portion 30 and/or can increase the user's confidence in proper handling of the applicator 10.

As shown herein, the gripping indicia can be visual indicia. Any visual indicia suitable from distinguishing the grip portion from the barrel portion and/or the plunger can be used, such as, e.g., color, such as, e.g., a contrasting color and/or a coordinating color, sheen, such as, e.g., a glossy or matte finish, shimmer, any type of mark, figure, picture, identification code, symbol, icon, pattern, text, such as, e.g., a word, number, nomenclature, sentence, or instruction, line, line segment, curved line, band, arrow, area of coloration, or any other printed indicia having a purpose of providing a signal or guide to the user.

In certain embodiments, visual indicia can be a color, such as, e.g., a color in a hue or shade that differs from the barrel portion and/or plunger of the applicator and/or a contrasting color. In certain embodiments, the visual indicia can be a contrasting color to the barrel portion and/or the plunger portion, such as, e.g., two different hues. Visual indicia of a contrasting color can be useful to quickly identify the grip portion to the user. In certain embodiments, the difference in color (i.e., $\Delta E^*$) between the first shade and the second shade can be at least about 3.5, at least about 6, at least about 12, at least about 18, at least about 24, at least about 30, or more. The $\Delta E^*$ can calculated by the formula $\Delta E^* = [(L^*_X - L^*_Y)^2 + (a^*_X - a^*_Y)^2 + (b^*_X - b^*_Y)^2]^{1/2}$, where 'X' and 'Y' are not the same measured point on the viewing surface. In addition or alternatively, the visual indicia can be a coordinating color to the barrel portion and/or the plunger portion, such as, e.g., two different shades of the same color, such as, e.g., a shade that can be considered pastel and a shade that can be considered bright. Visual indicia of a coordinating color can be useful to identify the grip portion to the user while communicating a soothing appearance, an appearance of fun, and/or a seasonal appearance.

The visual indicia can also be a pattern, such as, e.g., a printed, molded, adhered, hot stamped, screen printed, pressure sensitive label, therimage label, shrink sleeve, and/or painted pattern. In certain embodiments, the visual indicia can be a line or can provide the perception of a line, such as, e.g., a colored line, a patterned line, a broken line, or a foil line, that can be positioned to provide a gripping indicia, such as, e.g., to demarcate the grip portion from the barrel portion and/or the plunger portion.

As shown herein, the gripping indicia can be tactile indicia. Any tactile indicia suitable from distinguishing the grip portion from the barrel portion and/or the plunger can be used, such as, e.g., textures, embossments, raised printing, compressible material, such as, e.g., rubber, silicone, and/or foam, and/or other material that can increase the coefficient of friction of the grip portion. In certain embodiments, the tactile indicia can be a generally uniform texture, such as, e.g., a coating or additive applied to the grip portion, as compared to a generally discontinuous texture, such as, e.g., a series of ribs, ridges, or raised portions. Tactile indicia can, for example, distinguish the grip portion from the barrel portion and/or the plunger and/or can provide the user with improved applicator control and decreased finger slippage.

In certain embodiments, however, the grip portion can include one or more gripping indicia and one or more gripping structures, such as, e.g., ridges, ribs, grooves, and/or other gripping structures and/or one or more auditory signals, such as, e.g., a click. For example, in one embodiment, the grip portion can include a gripping indicia that is a visual indicia, such as, e.g., a color, and one or more gripping structures, such as, e.g., one or more ridges, and/or one or more auditory signals. In certain embodiments, the grip portion can include gripping indicia that include a first visual indicia, such as, e.g., a color, and a second visual indicia, such as, e.g., a sheen. Alternatively, or in addition, the grip portion can include gripping indicia that include a first visual indicia, such as, e.g., a color, one or more gripping structures, and a second visual indicia, such as, e.g., a second color, wherein the second color corresponds to the one or more gripping structures, for example, to provide a visual emphasis to the gripping structures. In certain embodiments, the grip portion can include gripping indicia that include a tactile indicia, such as, e.g., a texture, and one or more gripping structures, and/or one or more auditory signals. Alternatively, or in addition, the grip portion can include gripping indicia that include a visual indicia, such as, e.g., a color, a tactile indicia, such as, e.g., a texture, and one or more gripping structures, and/or one or more auditory signals.

The gripping indicia can be provided at any suitable location on or adjacent to the grip portion. In certain embodiments, one or more gripping indicia can be provided over substantially the entire surface, such as, e.g., when the grip portion is substantially entirely a color and/or texture, and/or when the grip portion is substantially entirely a combination of one or more gripping indicia. In addition, or alternatively, the gripping indicia can cover a portion of the grip portion, such as, e.g., more than about 10%, more than about 20%, more than about 30%, more than about 40%, more than about 50%, more than about 60%, more than about 70%, more than about 80%, more than about 90%, or more. In certain embodiments, one or more gripping indicia can be located on the barrel portion adjacent to the grip portion, such as, e.g., a line or pattern that can, for example, define the grip portion.

Any suitable number or combination of gripping indicia can be employed. In certain embodiments, the grip portion can have at least one gripping indicia, such as, e.g., at least two gripping indicia, at least three gripping indicia, at least four gripping indicia, at least five gripping indicia, or more. For example, in certain embodiments, the grip portion can have at least one visual indicia, such as, e.g., a color. In addition, or alternatively, the grip portion can have at least one tactile indicia, such as, e.g., a texture. In certain embodiments, the grip portion can have at least one visual indicia, such as, e.g., a color, and at least one tactile indicia, such as, e.g., a texture. The grip portion can also have at least two visual indicia, such as, e.g., a color and a sheen, and at least one tactile indicia, such as, e.g., a texture.

The gripping indicia can be made in any suitable manner, such as, e.g., by printing, stamping, embossing, injection molding, reforming, such as, e.g., via heat, dipping, such as, e.g., in a liquid solution, co-injection molding, taping, adhering, painting, screen printing, pressure sensitive labeling, hot stamping, therimage labeling, shrink sleeve, dimensional coating, combinations thereof, and/or any other suitable manner.

In certain embodiments, the grip portion can include at least one gripping indicia that communicates one or more properties of the applicator in addition to the location and/or benefits of the grip portion. Such properties can include, for example, absorbency, fragrance, product tier, such as, e.g., luxury tier, mid-tier, or basic, size, tampon benefits, or other properties. For example, in certain embodiments, the gripping indicia can correspond to absorbency, such as, e.g., a color corresponding to absorbency, for example, green for super absorbency, yellow for regular absorbency, purple for lite absorbency, and/or orange for super plus absorbency.

Gripping indicia can be used with any suitable applicator, such as, e.g., applicators having a grip portion. The grip portion can be a defined grip portion, such as, e.g., a grip portion having a shape and/or size differing from the barrel and/or a grip portion having gripping structures. Alternatively, the grip portion can be undefined but for the gripping indicia, such as, e.g., a barrel and grip portion having a substantially uniform cross-sectional shape with a color band defining the grip portion. In certain embodiments, gripping indicia can be provided to communicate information relating to the applicator function, such as, e.g., the ability of the grip portion to rotate relative to the barrel portion, such as, e.g., described in U.S. patent application Ser. No. 11/703,919, filed Feb. 7, 2007, low-placement applicators, biodegradable applicators, or any other suitable function. For example, in the case of an applicator where the grip portion can rotate relative to the barrel portion, gripping indicia can communicate to a user this ability, can communicate to the user where to place her fingers, and/or can improve control of the applicator such as, e.g., improving the user's grip and/or by reducing finger slipping.

An array of applicators is also provided. The array can include a first applicator having at least a first gripping indicia and a second applicator having at least a second gripping indicia. The applicators can have additional gripping indicia that are the same or different. For example, in certain embodiments, the first gripping indicia can be a visual indicia such as, e.g., a first color, and the second gripping indicia can be a visual indicia such as, e.g., a second color, and the first and second applicators can further have a tactile indicia such as, e.g., a texture, that is the same or different on each applicator. The first visual indicia can communicate a first characteristic and the second visual indicia can communicate a second characteristic, such as, e.g., by using signals familiar to the consumer, such as, e.g., colors, and/or by otherwise communicating a characteristic, such as, e.g., using colors increasing in brightness and/or darkness to denote greater absorbency, using colors increasing in sheen to denote higher tiers of products, or any other suitable signal. In certain embodiments, the characteristic can be absorbency, size, tier level, or any other characteristic. The array can be packaged in separate external packages or can be packaged in the same external package.

In certain embodiments, applicators can be packaged wrappers, such as, e.g., individually packaged in wrappers and/or in containers such as bags, boxes, or cartons, which can carry a similar visual indicia to aid a user in choosing an appropriate applicator or material contained therein for an appropriate function. For example, applicators having a gripping indicia that is a visual indicia can be packaged in wrappers and/or boxes or cartons bearing a visual signal or indicia that corresponds in visual distinction to the gripping indicia of the applicator. Thus, if the gripping indicia is a visual indicia that is a shade of color, visual indicia on the wrapper and/or package can be a matching or substantially-matching shade of color. By "substantially-matching" is meant the color is close enough that the gripping indicia and the wrapper and/or packaging can be easily matched by one comparing applicators and packaging. For example, substantially-matching shades can be matching within the range of normal variance of colors from lot to lot of ink, dye, or other color-inducing medium, or within normal variance due to slight differences perceived on film versus paper, and the like. Other means of obtaining corresponding visual distinction include matching the shapes, styles, or overall appearance of visual indicia with corresponding gripping indicia. Thus, in certain embodiments, a consumer or user of feminine hygiene articles can choose a feminine hygiene article employing an applicator of the present invention and having a desired functional characteristic more easily based on the wrapper and/or packaging, with a confirmation or reinforcement of that functional characteristic on each applicator inside the wrapper and/or packaging. In certain embodiments, the applicator can be individually packaged in a wrapper and a plurality of wrapped applicators can be packaged in a box and/or carton. The wrapped applicators may or may not be visible to the consumer through a window in the package.

The barrel portion can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, polyhydroxyalkanoate, ethylene vinyl acetate, polyurethane, silicone, thermoplastic starch, trans-poly isoprene, derivatives thereof, copolymers thereof, mixtures thereof, or any suitable smooth plastic material. Examples of suitable materials are disclosed in, e.g., U.S. Pat. Nos. 5,346,468 and 5,558,631. In certain embodiments, additives can be included in the material to alter or enhance certain material properties. Suitable additives include, for example, mold release agents, slip agents, surface energy modifiers, inorganic fillers and/or any other suitable additives. In certain embodiments, the barrel portion can be coated with a substance to give it a high slip characteristic, such as, e.g., with wax, polyethylene, a combination of wax and polyethylene, cellophane, clay, and other lubricants that can facilitate comfortable insertion.

The barrel portion can be sized and configured to house a feminine hygiene product, such as, e.g., an absorbent tampon and/or pessary. In certain embodiments, the size of the barrel portion can be determined primarily by the dimensions of the feminine hygiene product. For example, the barrel portion can have inner diameters of about 5.0 millimeters to about 22.0 millimeters and a wall thickness of about 0.2 millimeter to about 2.0 millimeters. The inner diameter of the barrel portion can be greater than the diameter of the feminine hygiene product to prevent the barrel portion from interfering with the expulsion of the feminine hygiene product from the barrel portion. In certain embodiments, the inner diameter of the barrel portion can have varying diameters and shapes to conform to the profiled shape of the enclosed feminine hygiene product, such as, e.g., a tampon. The barrel portion can have a length sufficient to house the feminine hygiene product prior to the expulsion of the feminine hygiene product from the applicator into the vagina.

The barrel portion can be of any suitable cross-sectional shape. In certain embodiments, the barrel portion can include a generally non-circular cross-sectional shape, such as, e.g., oval, rectangular, elliptical, oblate, or other suitable shapes. The barrel portion can have a cross-sectional shape that has a greater thickness than width or vice versa. In certain embodiments, the barrel portion can have a substantially uniform cross-section, such as, e.g., having the same cross-section along the length. In other embodiments, the barrel portion can have varying cross-sectional shapes and/or cross-sectional sizes, such as, e.g., a barrel portion having a smaller cross-sectional area near the insertion end of the barrel and a larger cross-sectional area near the opposite end.

The insertion end of the barrel portion can be open-end or closed-ended. In certain embodiments, the insertion end of the barrel portion can include petals, corrugations, pleats, a film cap, or other means for covering the barrel portion prior to explusion of the tampon. In certain embodiments, the material, such as, e.g., a feminine care product can be loaded into the barrel portion prior to covering the insertion end of the barrel portion. Alternatively, the insertion end of the barrel portion can be covered prior to loading the feminine hygiene product into the barrel portion.

The grip portion can be constructed from any suitable material. The barrel portion can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, polyhydroxyalkanoate, ethylene vinyl acetate, polyurethane, silicone, thermoplastic starch, trans-poly isoprene, derivatives thereof, copolymers thereof, mixtures thereof, or any suitable smooth plastic material. In certain embodiments, additives can be included in the material to alter or enhance certain material properties. Suitable additives include, for example, mold release agents, slip agents, surface energy modifiers, pearlescent agents, inorganic fillers, and/or any other suitable additives. In certain embodiments, the grip portion can be a same material as the barrel portion. Alternatively, the grip portion can be one or more different materials as compared to the barrel portion. The grip portion can also comprise one or more compressible materials, such as, e.g., rubber, silicone, and/or foam, and/or one or more soft plastics. In certain embodiments, the grip portion can have a substantially rigid inner surface and a deformable outer surface, such as, e.g., to improve user comfort while substantially preventing compression of the interior of the grip, such as, e.g., to allow the plunger to move in the axial direction while the outer surface of the grip is deformed by a user's fingers.

The grip portion can provide for secure handling of the applicator. The perimeter of the grip portion can be any suitable shape, such as, for example, oval, circular, arc, concave, cone convex, diamond, line, polygon, rib, square, triangle, rectangular, or any combination thereof. The grip portion can include projections, depressions, texturing, embossments, grooves, treads, and/or raised surfaces. Such surfaces can be created by impressing or compressing the surfaces. In certain embodiments, the grip portion can include one or more flattened sides and/or one or more spaces for a decorative marking or a character. In addition, or alternatively, the surfaces of the grip portion can include a material that can provide a frictional resistance for the user's fingers during the insertion of the tampon applicator into the body. Suitable materials that can provide friction include, for example, abrasive materials, high wet coefficient of friction materials, pressure sensitive adhesives, or any combinations thereof. In certain embodiments, the surfaces of the grip portion can include a material that can improve the feel of the grip to a user, such as, e.g., one or more compressible materials, such as, e.g., rubber, silicone, and/or foam. In certain embodiments, the grip portion shape can correspond to the barrel portion shape. Alternatively, the grip portion can be a different shape than the barrel portion.

The plunger can be constructed from any suitable material. The barrel portion can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, polyhydroxyalkanoate, ethylene vinyl acetate, polyurethane, silicone, thermoplastic starch, trans-poly isoprene, derivatives thereof, copolymers thereof, mixtures thereof, or any suitable smooth plastic material. Suitable plungers are disclosed in, e.g., U.S. Pat. No. 5,346,468 and U.S. Pat. No. 5,558,631. In certain embodiments, additives can be included in the material to alter or enhance certain material properties. Suitable additives include, for example, mold release agents, slip agents, surface energy modifiers, pearlescent agents, inorganic fillers, and/or any other suitable additives.

The plunger can be hollow or solid. In certain embodiments, the plunger can have a hollow interior, a first end, and a second end opposed to the first end. The first end is the portion of the plunger that pushes against the tampon during the expulsion of the tampon from the barrel portion. The second end is the portion of the plunger in which the axial force is applied to expel the tampon from the barrel portion. In certain embodiments, the plunger can have a locking mechanism, such as, e.g., a locking mechanism that retains the plunger within the barrel portion and/or grip portion of the applicator prior to depression of the plunger and expulsion of the tampon. Examples of such locking mechanisms are described in, for example, U.S. Pat. Nos. 6,019,744 and 6,450,986.

In certain embodiments, the plunger can be an optional component for use with the applicator. For example, the applicator can be fully functional if the plunger is omitted, i.e., if a user must insert and push the feminine hygiene product through the tampon applicator digitally.

In certain embodiments, at least a portion of the applicator can contact and/or conform to at least a portion of the surface of the tampon. Rigid insertion end structures can be shaped in a suitable manner, such as, e.g., by injection molding, or by reshaping in a secondary process to provide at least a degree of profiled shape observation. Alternatively, insertion ends of applicators made from flexible or pliable materials, such as films, paper and flexible wovens or non-wovens, can also be used. Such flexible or pliable insertion ends include those which partially or fully enclose the tampon comprising a "sleeve" or a "tube," such as, e.g., in U.S. Pat. Nos. 2,922,422 and 2,922,423; a "sheath," such as, e.g., in U.S. Pat. Nos. 2,092,427 and 3,749,093; a "barrel," such as, e.g., in U.S. Pat. No. 5,135,475; a "bag," such as, e.g., in U.S. Pat. No. 3,358,686; or a "film enclosure," such as, e.g., in U.S. Pat. No. 4,610,659.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator for feminine care products, the applicator comprising:
   a. a barrel portion;
   b. a grip portion positioned adjacent the barrel portion; and
   c. gripping indicia associated with at least a part of the grip portion, the gripping indicia comprising at least two visual indicia and at least one tactile indicia for distinguishing the grip portion from the barrel portion, wherein one of the at least two visual indicia is selected from the group consisting of color, color shade, and color hue, and wherein the other of the at least two visual indicia is sheen; and wherein the gripping indicia do not extend into the barrel portion.

2. The applicator of claim 1, wherein the sheen is glossy or matte.

3. The applicator of claim 1, wherein the at least one tactile indicia is at least partially defined by employment of a different material in the grip portion than that in the barrel portion.

4. The applicator of claim 1, wherein the at least one tactile indicia is at least partially defined by employment of gripping structures on the grip portion.

5. The applicator of claim 4, wherein the gripping structures comprise projections or raised surfaces extending outwardly from the grip portion.

6. The applicator of claim 3, wherein the different material comprises a material selected from the group consisting of a polystyrene, a polyamide, a nylon, a polyurethane, a silicone, and a rubber.

7. An applicator for feminine care products, the applicator comprising:
  a. a barrel portion;
  b. a grip portion positioned adjacent the barrel portion; and
  c. gripping indicia associated with at least a part of the grip portion, the gripping indicia comprising:
    i. a first visual indicia selected from the group consisting of color, color shade, and color hue;
    ii. a second visual indicia comprising sheen;
    iii. a first tactile indicia defined by employment of a different material in the grip portion than that in the barrel portion; and
    iv. a second tactile indicia defined by gripping structures;
  and wherein the gripping indicia do not extend into the barrel portion.

8. The applicator of claim 7, wherein the gripping structures are selected from the group consisting of projections, depressions, embossments, grooves, treads, raised surfaces, and combinations thereof.

9. An applicator for feminine care products, the applicator comprising:
  a. a barrel portion;
  b. a grip portion positioned adjacent the barrel portion; and
  c. gripping indicia associated with at least a part of the grip portion, the gripping indicia comprising:
    i. a first visual indicia selected from the group consisting of first color, first color shade, and first color hue;
    ii. a second visual indicia selected from the group consisting of second color, second color shade, and second color hue;
    iii. a first tactile indicia defined by employment of a different material in the grip portion than that in the barrel portion; and
    iv. a second tactile indicia defined by gripping structures.

10. The applicator of claim 9, wherein the gripping structures are selected from the group consisting of projections, depressions, embossments, grooves, treads, raised surfaces, and combinations thereof.

* * * * *